United States Patent
Leighton et al.

(10) Patent No.: US 12,303,523 B2
(45) Date of Patent: May 20, 2025

(54) METHOD FOR TREATING DUPUYTREN'S DISEASE

(71) Applicant: Dale Biotech, LLC, Kennedale, TX (US)

(72) Inventors: Anton Leighton, Oakland, CA (US); Ralph T. Salvagno, Hancock, MD (US)

(73) Assignee: DALE BIOTECH, LLC, Oakland, CA (US)

( * ) Notice: Subject to any disclaimer, the term of this patent is extended or adjusted under 35 U.S.C. 154(b) by 748 days.

(21) Appl. No.: 17/457,524

(22) Filed: Dec. 3, 2021

(65) Prior Publication Data
US 2022/0088047 A1 Mar. 24, 2022

Related U.S. Application Data

(63) Continuation of application No. PCT/US2020/036405, filed on Jun. 5, 2020.

(60) Provisional application No. 62/858,752, filed on Jun. 7, 2019.

(51) Int. Cl.
*A61K 31/7028* (2006.01)
*A61K 31/609* (2006.01)
*A61P 19/02* (2006.01)

(52) U.S. Cl.
CPC ........ *A61K 31/7028* (2013.01); *A61K 31/609* (2013.01); *A61P 19/02* (2018.01)

(58) Field of Classification Search
None
See application file for complete search history.

(56) References Cited

U.S. PATENT DOCUMENTS 7,262,171 B1 8/2007 Piljac et al.
11,033,518 B2 * 6/2021 Yook .................. A61K 31/167

2011/0123623 A1 5/2011 Desanto
2016/0158325 A1 6/2016 Larsen
2016/0280775 A1 9/2016 Nanchahal et al.

FOREIGN PATENT DOCUMENTS

| CN | 105326848 A | 2/2016 |
| WO | 1999043334 A1 | 9/1999 |
| WO | 2012177593 A3 | 12/2012 |

OTHER PUBLICATIONS

Li, Molecular Medicine Reports 19: 2808-2816, 2019. (Year: 2019).*
International Search Report for PCT Application No. PCT/US2020/036405. Mail Date: Sep. 3, 2020. 2 pages.
European Patent Office (EPO), Extended European Search Report, EP No. 20818765.8, Sep. 25, 2023.
Hurst, Lawrence C et al., Injectable collagenase clostridium histolyticum for Dupuytren's contracture, New England Journal of Medicine, Massachusetts Medical Society, vol. 361, No. 10, Sep. 3, 2009, pp. 968-979, DOI:10.1056/NEJOA0810866.
Hunter, David J et al., Osteoarthritis, The Lancet, vol. 393, No. 10182, Apr. 27, 2019, pp. 1745-1759, DOI:10.1016/S0140-6736(19)30417-9.
Georgiannos, Dimitrios et al., Adhesive Casulitis of the Shouler. Is there Consensus Regarding the Treatment? A Comprehensive Review, The Open Orthopaedics Journal, vol. 11, No. 1, Feb. 28, 2017, pp. 65-76, DOI:10.2174/1874325001711010065.

* cited by examiner

*Primary Examiner* — Layla D Berry
(74) *Attorney, Agent, or Firm* — Perkins Coie LLP; Viola Kung

(57) ABSTRACT

The present invention is directed to methods for treating Dupuytren's disease, osteoarthritis, and adhesive capsulitis. The method comprises the steps of identifying a subject in need thereof, and administering to the subject an effective amount of one or more rhamnolipids, optionally in combination with niclosamide. A pharmaceutical composition comprising rhamnolipids, optionally in combination with niclosamide or a salt thereof, can be applied by any accepted mode of administration including oral, topical, or injection within or around the affected body part such as an affected hand, knee, or shoulder.

8 Claims, 2 Drawing Sheets

METHOD FOR TREATING DUPUYTREN'S DISEASE

This application is a continuation of PCT/US2020/036405, filed Jun. 5, 2020; which claims the benefit of U.S. Provisional Application Nos. 62/858,752, filed Jun. 7, 2019. The contents of the above-identified applications are incorporated herein by reference in their entirety.

FIELD OF THE INVENTION

The present invention relates to treating Dupuytren's disease, osteoarthritis, and adhesive capsulitis, with rhamnolipids, optionally in combination of niclosamide.

BACKGROUND OF THE INVENTION

Dupuytren's disease (palmar fibromatosis; Dupuytren's contracture) is a disease associated with the buildup of extracellular matrix materials such as collagen in the connective tissue characterized by thickening of the palmar fascia of the hand. The connective tissue thickens and shortens with the physical effect of causing the fingers to curl, most commonly the ring finger and little finger. Dupuytren's disease is a complex fibro-proliferative disorder of the hand that is often progressive and eventually can cause contractures of the affected fingers.

Dupuytren's disease is characterized by thickening and contracture of the fascia (connective tissue) of the palm, usually progressing to flexion deformities and involvement of one or more fingers. This results from formation of longitudinal cords of indurated fibrous tissue in the palm and extending into the finger. A similar lesion sometimes occurs in the foot (Ledderhose's Disease).

Dupuytren's disease affects approximately 5% of the white Caucasian population. The most common manifestation is progressive flexion contracture of the fingers, resulting in significantly compromised function. The causes of Dupuytren's disease are not well understood and underlying disease is not currently curable.

Transforming growth factor beta (TGF-β) has been implicated as a key stimulator of myofibroblast activity and fascial contraction in Dupuytren's disease. TGF-β shows an intense intracellular marking pattern associated with fibroblasts, myofibroblasts, and capillary endothelial cells in all Dupuytren's samples, regardless of disease stage. (Badalamente M A et al, J Hand Surg Am., 1996, 21:210-5)

Treatment of Dupuytren's disease has traditionally involved surgical excision of the offending tissue. In severe or recurrent disease, the surgical excision may be combined with excision of the overlying palmar skin and resurfacing of the cutaneous defect with full-thickness skin graft. Surgery is typically followed by prolonged rehabilitation, usually lasting 3 months and complications have been reported in up to 20% of cases. Such surgical correction is the mainstay treatment of later stage disease when secondary changes to tendons and joints have developed. A less invasive surgical intervention is needle aponeurectomy in which the fibrous bands (contractures) in connective tissue are divided using the bevel of a needle.

Enzymatic cleavage of the affected tissue has been the focus of development to reduce invasiveness associated with surgery and improve recovery time of surgical treatment. Clostridial collagenase, a bacterial collagenase, has been granted FDA approval as Xiaflex®. U.S. Pat. No. RE39,941, U.S. Pat. Nos. 5,589,171 and 6,086,872 describe the use of bacterial collagenase for the enzymatic cleavage of connective tissue in the treatment of Dupuytren's disease. Xiaflex® is associated with high cost, possible allergic reactions and development of neutralizing antibodies.

Bacterial collagenase therapy has been associated with improved outcomes in the treatment of Dupuytren's disease when injected into the affected areas of contractures, but it is expensive and is associated with development of neutralizing antibodies.

Osteoarthritis (OA) is a potentially debilitating degenerative disease of the joints characterized by cartilage degeneration. Although multifactorial in origin, there is clear evidence that OA has an inflammatory component. Strategies such as weight loss and bracing, directed at mitigating biomechanical factors, do little to alter disease progression. Non-steroidal anti-inflammatory medications (NSAIDS), directed at reducing inflammation associated with cartilage breakdown, are only moderately effective and are associated with potential cardiovascular, gastrointestinal and hematologic complications.

Nuclear factor-kappa B (NF-κB) is recognized as a disease contributing factor and therapeutic target for OA (Choi M-C et al, Cells, 2019; 8:734). Wang et al have identified signal transducer and activator of transcription 3 (STAT3) as a key mediator of the NF-κB signaling pathway. Wang et al also report that STAT3, through its interaction with Smad3, attenuates TGF-β. (Wang, G. et al, Oncogene, 2016; 35: 4388-4398). STAT3 is the core transcription factor and promotes the development of osteoarthritis through the signaling of NF-κB. (Wang W, et al, Exp Ther Med. 2020, 19: 722-728.)

TGF-β is crucial to maintaining homeostasis of articular cartilage and subchondral bone. However, aberrant activation of TGF-β in the subchondral bone in response to an abnormal mechanical loading environment induces formation of osteoid islets at the onset of OA. As a result, alteration of subchondral bone structure changes the stress distribution on the articular cartilage and leads to its degeneration. Thus, inhibition of TGF-β activity in the subchondral bone may provide a new avenue of treatment for OA (Zhen G. et al, Trends in Pharmacologic Sciences, 2014; 35:227-236).

The causes of OA are still unknown and there is much debate in the literature as to the exact sequence of events that trigger the onset of the heterogeneous disease we recognize as OA. There is currently no consensus model for OA that naturally reflects human disease. Existing ex-vivo models do not incorporate the important inter-tissue communication between joint components required for disease progression and differences in size, anatomy, histology and biomechanics between different animal models makes translation to the human model very difficult. (Cope P J, et al, Osteoarthritis Cartilage, 2019, 27: 230-239)

Adhesive capsulitis (AC), also known as "frozen shoulder", is characterized by the gradual loss of glenohumeral motion with chronic inflammation and capsular fibrosis. Adhesive capsulitis affects approximately 2%-5% of adults between the age of 40-70 and can be quite disabling in terms of occupational requirement and performance of activities of daily living. Conservative treatment including observation, physical therapy, and intra-articular injections of corticosteroid can be beneficial, but recalcitrant cases may require surgery. In many cases it can take months, if not years, until tangible resolution is observed. Arthroscopic and open capsular release carry the risk of bone fractures, tendon and labrum tears, infection and neurovascular injury. Avoidance of surgical risk by providing a biologic approach is not currently part of the treatment modalities available.

Adhesive capsulitis is poorly understood, particularly its underlying etiology. Microscopic examination of tissue from AC sufferers reveals fibroblasts mixed with type I and type III collagen, which has led to AC generally being regarded as a disorder like Dupuytren's disease. The advancement of the condition seems to be due to the presence of adhesion-related cytokines, including TGF-β. (Rodeo, S A, et al, Journal of Orthopaedic Research, 2016, 15: 427-436).

Lho et al report significantly greater expression of inter-leukin-1a and other inflammatory cytokines in the joint capsule of patients with frozen shoulder. (Lho Y M et al, Journal of Shoulder and Elbow, 2013, 22: 666-672). Inhibiting TGF-β signaling may a promising therapeutic intervention. (Usher, K. M., et al, Bone Res., 2019, 7: 1-24).

Originally published in 1996 in the American Journal of Industrial Medicine, the Disabilities of the Arm, Shoulder, and Hand (DASH) was a collaborative initiative between the American Academy of Orthopaedic Surgeons, the Council of Musculoskeletal Specialty Societies, and the Institute for Work and Health. This outcome measure is designed to be a standardized assessment of the impact on function of a variety of musculoskeletal disease and injuries in the upper extremity. The DASH is a 30-item self-reported questionnaire in which the response options are presented as 5-point Likert scales. Scores range from 0 (no disability) to 100 (most severe disability). This score was designed be useful in patients with any musculoskeletal disorder of the upper limb.

The Western Ontario and McMaster Universities Arthritis Index (WOMAC) is widely used in the evaluation of Hip and Knee Osteoarthritis. It is a self-administered questionnaire consisting of 24 items divided into 3 subscales:

Pain (5 items): during walking, using stairs, in bed, sitting or lying, and standing upright.

Stiffness (2 items): after first waking and later in the day.

Physical Function (17 items): using stairs, rising from sitting, standing, bending, walking, getting in/out of a car, shopping, putting on/taking off socks, rising from bed, lying in bed, getting in/out of bath, sitting, getting on/off toilet, heavy domestic duties, light domestic duties.

There remains a need for a cost-effective and well-tolerated therapeutic intervention for treating and inhibiting progression of Dupuytren's disease, osteoarthritis and adhesive capsulitis.

DETAILED DESCRIPTION OF THE INVENTION

Figure 1:
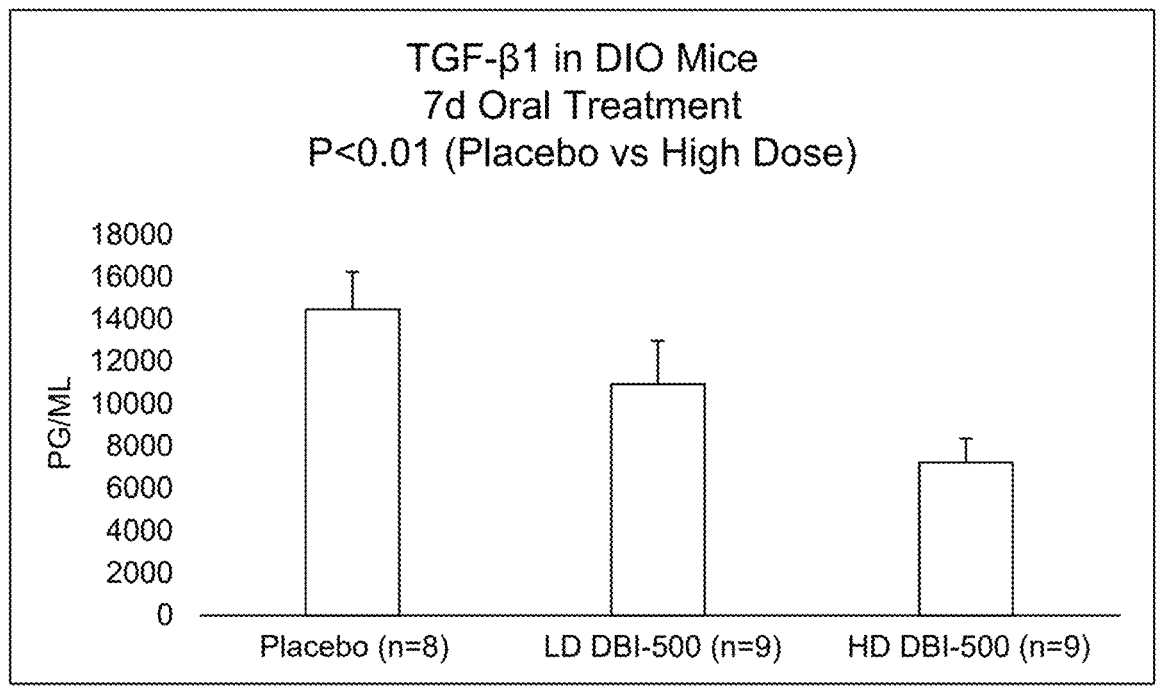
FIG. 1 shows beneficial effects of di-rhamnolipids on blood level of TGF-β in C57BL6 mice with diet-induced obesity after 7 days of oral dosing of a rhamnolipid formulation composed predominantly of di-rhamnolipid C10-C10. Mean daily doses for the LD and HD groups were 51 mg/kg and 103 mg/kg, respectively. The results show a dose dependent significant decrease in TGF-β after 7 days of oral treatment with DR (di-rhamnolipid). P<0.01 in placebo vs. high dose.

The present invention relates to methods for treating Dupuytren's disease, osteoarthritis, and adhesive capsulitis. The inventors have discovered that injection of rhamnolipids in a minipig disrupt fibrous collagen bands in subcutaneous tissue. Subcutaneous fibrous bands contain collagen I and collagen III, as do the nodes and fibers associated with Dupuytren's disease.

Rhamnolipids reduce collagen associated with Dupuytren's disease and are effective to treat contractures associated with Dupuytren's disease. Rhamnolipids, optionally in combination with niclosamide, are effective for inhibiting development and progression of contractures in Dupuytren's disease associated with increased collagen production.

Rhamnolipids, optionally in combination with niclosamide, modulate the effect of pro-inflammatory cytokines associated with osteoarthritis. Rhamnolipids, optionally in combination with niclosamide, are effective in improving one or more of the pathologic conditions associated with osteoarthritis including cartilage destruction, joint stiffness, effusion and capsular inflammation.

Rhamnolipids, optionally in combination with niclosamide, modulate the effect of pro-inflammatory cytokines associated with adhesive capsulitis. Rhamnolipids, optionally in combination with niclosamide, are effective in improving one or more of the pathologic conditions associated with adhesive capsulitis including capsular inflammation and capsular contracture.

Rhamnolipids

Rhamnolipids are composed of rhamnose sugar molecules and β-hydroxyalkanoic acids. Rhamnolipids suitable to be used in the present invention include natural rhamnolipids, for example, obtained from *Pseudomonas aeruginosa*; rhamnolipids produced by any pseudomonad, including *P. chlororaphis, Burkholdera pseudomallei*, Burkholdera (*Pseudomonas*) *plantarii*, and any recombinant Pseudomonad. Suitable rhamnolipids also include those produced by other bacteria or by plants either naturally or through (genetic) manipulation.

Suitable rhamnolipids for this invention include rhamnolipids and their analogs prepared by chemical synthesis or expression by mammalian cells. Suitable rhamnolipids include those disclosed in U.S. Pat. Nos. 7,262,171 and 5,514,661, in which the structures of rhamnolipids are incorporated herein by reference.

Useful rhamnolipids for this invention further include those defined in the publication Abdel-Mawgoud, A. M., et al, Appl Microbiol Biotechnol. 2010, 86(5): 1323-1336 and Bauer, J. et al, Chem. Eur. J. 2006, 12: 7116-7124, in which the structures of rhamnolipids are incorporated herein by reference.

Suitable rhamnolipid formulations contain one or more rhamnolipids of formula (I)

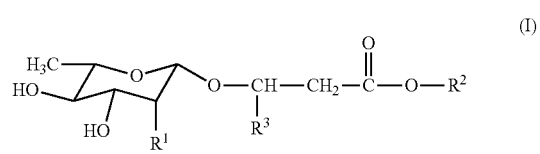

wherein:
R¹=H, unsubstituted α-L-rhamnopyranosyl, α-L-rhamnopyranosyl substituted at the 2 position with a group of formula —O—C(=O)—CH=CH—R⁵;
R²=H, $C_{1-6}$alkyl, —CHR⁴—CH₂—COOH, —CHR⁴—CH₂—CH₂OH, or —CHR⁴—CH₂—COOR⁶; and
R³-R⁶ are independently alkyl.

"Alkyl" refers to groups of from 1 to 12 carbon atoms, either straight chained or branched, preferably from 1 to 8 carbon atoms, and more preferably 1 to 6 carbon atoms.

In one embodiment, $R^3$=—$(CH_2)_x$—$CH_3$, wherein x=4-19, such as 8, 9, 10, and 11.

In one embodiment, $R^4$=—$(CH_2)_y$—$CH_3$, wherein y=1-19, such as 8, 9, 10, and 11.

In one embodiment, $R^5$=—$(CH_2)_z$—$CH_3$, wherein z=1-12; and $R^6$=—$C_{1-6}$alkyl, In one embodiment, R¹=α-L-rhamnopyranosyl substituted at the 2-position by —O—C(=O)—CH=CH—R⁵, R²=—CHR⁴—CH₂—COOH or =—CHR⁴—CH₂—COOCH₃, R³=—(CH₂)₅—CH₃, R⁴=—(CH₂)₂—CH₃ or —(CH₂)₅—CH₃, and R⁵=—(CH₂)₅—CH₃.

Useful rhamnolipids of the Formula I include di-rhamnolipids as shown in Formula II below.

Formula II

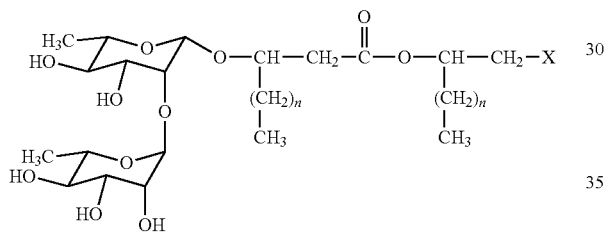

Wherein n is an integer, which independently equals to 4-12, e.g., n=6, 8, or 10, and X=COOH or CH₂OH.

The structure of di-rhamnolipid α-rhamnopyranosyl-(1,2)-α-L-ramnopyranosyl)-3-hydroxydecanoyl-3-hydroxydecanoic acid (Rha-Rha-C10-C10) is illustrated below (Formula a):

Formula a

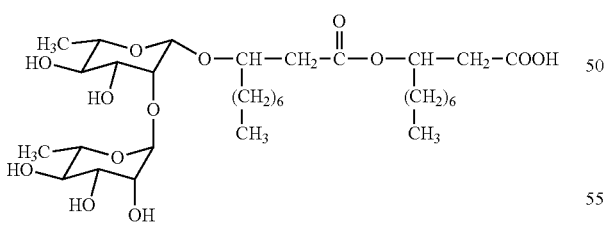

Preferred rhamnolipids are L-rhamnosyl-β-hydroxydecanoyl-β-hydroxydecanoate (mono-rhamnolipid, Rha-C10-C10) and L-rhamnosyl-L-rhamnosyl-β-hydroxydecanoyl-β-hydroxydecanoate (di-rhamnolipid, Rha-Rha-C10-C10), and the mixture thereof.

Additional preferred di-rhamnolipids for this invention include: L-rhamnopyranosyl-L-rhamnopyranosyl-β-hydroxydecanoyl-β-hydroxydodecanoate (often referred to as Rha-Rha-C10-C12); L-rhamnopyranosyl-L-rhamnopyranosyl-β-hydroxytetradecanoyl-β-hydroxytetradecanoate (often referred to as Rha-Rha-C14-C14). In general, di-rhamnolipids suitable for this invention include Rha-Rha-A-B, where A and B are independently C10, C12, C14, C16, and C18.

Preferred rhamnolipids also include the following four rhamnolipids: RL-1,2₁₄₋₁₄CH₂OH, RL-2,2₁₄₋₁₄CH₂OH, RL-1,3₁₄₋₁₄COOH, and RL-1,2₁₄₋₁₄COOH.

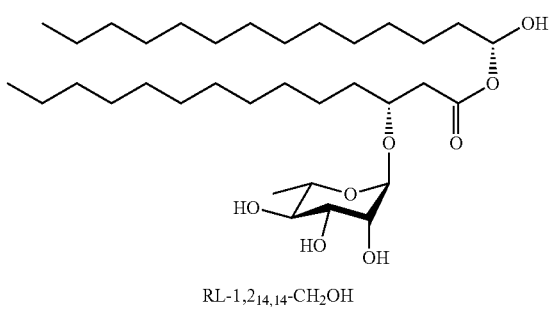

RL-1,2₁₄,₁₄-CH₂OH

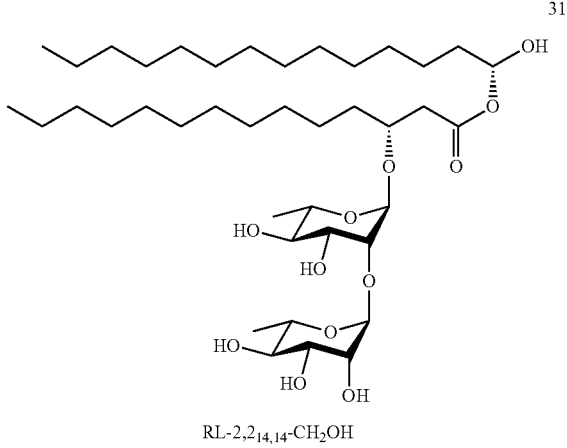

RL-2,2₁₄,₁₄-CH₂OH

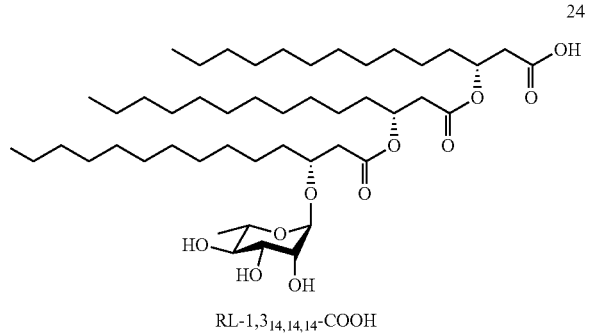

RL-1,3₁₄,₁₄,₁₄-COOH

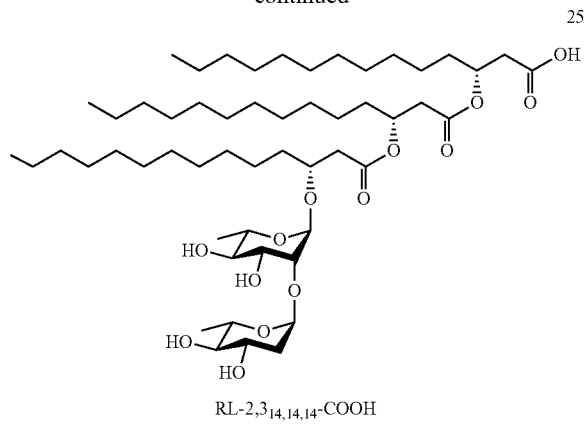

RL-2,3₁₄,₁₄,₁₄-COOH

Niclosamide

Niclosamide is an orally bioavailable chlorinated salicylanilide, approved as an anthelmintic drug (antiparasitic drug), which expels parasitic worms (helminths) and other internal parasites from the body by either stunning or killing them without causing significant damage to the host. Niclosamide, sold under the brand name Niclocide among others, is a oral medication used to treat tapeworm infestations.

Niclosamide has a molar weight of 327.119 g/mol, and has the following structure:

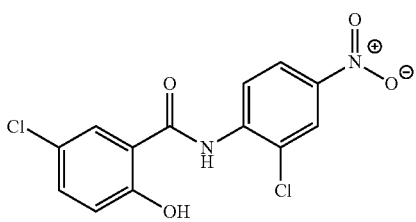 [SMILES: O=C(Nc1ccc([N+](=O)[O-])cc1Cl)c1cc(Cl)ccc1O]

Niclosamide useful for the present invention including niclosamide or a salt thereof such as niclosamide ethanolamine.

Niclosamide inhibits nuclear factor kappa-light-chain-enhancer of activated B cells (NF-κB) transcription, its binding to DNA, tumor necrosis factor (TNF)-induced phosphorylation of IκBα, translocation of p65 into the nucleus, and expression of NF-κB-regulated downstream genes in in vitro experiments. NF-κB is a transcription factor that induces the expression of proinflammatory cytokines. By inhibiting NF-κB, niclosamide inhibits inflammation.

Signal transducer and activator of transcription STAT3 plays a central role in the host response to injury. It is activated rapidly within cells by many cytokines, leading to pro-proliferative and pro-survival programs, with persistent activation, however, chronic inflammation and fibrosis ensue, leading to a number of debilitating diseases. (Kasembeli M M, et al. Int J Mol Sci. 2018 August; 19(8): 2299.)

Niclosamide potently inhibits the activation and transcriptional function of STAT3. (Ren X, et al. ACS Med Chem Lett., 2010, 1(9): 454-459.)

The very limited bioavailability of niclosamide is a major impediment to its development as a drug. Niclosamide is not very water soluble, its water solubility is only 0.005-0.008 mg/mL at 20° C. Niclosamide is sparingly soluble in ether, ethanol (22 mM), chloroform, acetone and DMSO (up to 10 mM). The ethanolamine salt dissolves in distilled water 0.18-0.28 mg/mL at 20° C.

The inventors have discovered that in the presence of rhamnolipids, niclosamide increases its water solubility by at least 2-4 fold. Treating Dupuytren's disease, osteoarthritis, or adhesive capsulitis with the combination of rhamnolipids and niclosamide provides advantages of a broad spectrum of activity against inflammatory cytokines that have been associated with these diseases.

Pharmaceutical Compositions

One or more rhamnolipids, optionally with niclosamide or a niclosamide salt, which are the active ingredient of the present invention, can be used as a pharmaceutical composition. One or more rhamnolipids can also be formulated in a pharmaceutical composition which comprises rhamnolipids and one or more pharmaceutically acceptable carriers. The pharmaceutical composition can be in the form of a liquid, a solid, or a semi-solid.

Pharmaceutically acceptable carriers can be selected by those skilled in the art using conventional criteria. Pharmaceutically acceptable carriers include, but are not limited to, sterile water or saline solution, aqueous electrolyte solutions, isotonicity modifiers, water polyethers such as polyethylene glycol, polyvinyls such as polyvinyl alcohol and povidone, cellulose derivatives such as methylcellulose and hydroxypropyl methylcellulose, polymers of acrylic acid such as carboxypolymethylene gel, nanoparticles, polysaccharides such as dextrans, and glycosaminoglycans such as sodium hyaluronate and salts such as sodium chloride and potassium chloride. A preferably pharmaceutically acceptable carrier is water or saline.

In one embodiment, the pharmaceutical composition of the present invention provides an aqueous solution comprising water and rhamnolipids; the composition optionally comprises suitable ionic or non-ionic tonicity modifiers, suitable buffering agents, and rhamnolipids. In one embodiment, the rhamnolipid is at 0.1-50% (w/w), optionally with 0.1-4 mg/mL of niclosamide, and the aqueous solution has a tonicity of 200-400 mOsm/kG and a pH of 4-9.

The pharmaceutical composition is preferably formulated to have a pH between 4.5-8, more preferably 5-7.4. The pharmaceutical composition may optionally contain a buffer to facilitate a stable pH of 5-7.4.

The pharmaceutical composition optionally contains non-ionic tonicity agents such as mannitol, sucrose, dextrose, glycerol, polyethylene glycol, propylene glycol, or ionic tonicity agent such as sodium chloride. The pharmaceutical composition can further contain ionic or non-ionic surfactants, bile salts, phospholipids, cyclodextrins, micelles, liposomes, emulsions, polymeric microspheres, nanoparticles, other biodegradable microsphere technology, or their combination.

In one embodiment, the pharmaceutical composition is in a dosage form such as tablets, capsules, granules, fine granules, powders, syrups, suppositories, injectable solutions, or the like. The above pharmaceutical composition can be prepared by conventional methods.

For example, a tablet formulation or a capsule formulation may contain other excipients that have no bioactivity and no reaction with rhamnolipids. Excipients of a tablet may include fillers, binders, lubricants and glidants, disintegrators, wetting agents, and release rate modifiers. Binders promote the adhesion of particles of the formulation and are important for a tablet formulation. Examples of binders include, but not limited to, carboxymethylcellulose, cellulose, ethylcellulose, hydroxypropylmethylcellulose, methylcellulose, karaya gum, starch, starch, and tragacanth gum, poly(acrylic acid), and polyvinylpyrrolidone. A tablet formulation may contain 1-90% of rhamnolipids. A capsule formulation may contain 1-100% of rhamnolipids.

In another embodiment, the pharmaceutical composition comprises one or more rhamnolipids imbedded in a solid or semi-solid matrix, and is in a liquid, solid, or semi-solid form. The pharmaceutical composition can be injected subcutaneously into the affected area of a subject and then the active ingredients slowly released in the subject. The formulation may contain 1-30% rhamnolipids. The application can be imbedded in a solid or semi-solid matrix, and is in a liquid, solid, or semi-solid form at time point of application.

In another embodiment, the pharmaceutical composition comprises one or more rhamnolipids that is applied topically to the palmar region of the hand, or the knee, or the shoulder, and thus directly over the affected areas. The formulation may contain 1-50%, or 5-50% rhamnolipids, and optionally 0.1-4 mg/mL niclosamide.

Topical formulations including rhamnolipid, optionally niclosamide, can be in a form of gel, cream, lotion, liquid, emulsion, ointment, spray, solution, and suspension. The inactive ingredients in the topical formulations for example include, but not limited to, diethylene glycol monoethyl ether (emollient/permeation enhancer), DMSO (solubility enhancer), silicone elastomer (rheology/texture modifier), caprylic/capric triglyceride, (emollient), octisalate, (emollient/UV filter), silicone fluid (emollient/diluent), squalene (emollient), sunflower oil (emollient), and silicone dioxide (thickening agent).

The pharmaceutical composition is preferred to be stable at room temperature for at least 6 months, 12 months, preferably 24 months, and more preferably 36 months. Stability, as used herein, means that rhamnolipid maintains at least 80%, preferably 85%, 90%, or 95% of its initial activity value.

The pharmaceutical compositions of the present invention can be prepared by aseptic technique. The purity levels of all materials used in the preparation preferably exceed 90%.

Methods of Use

The present invention is directed to a method for treating Dupuytren's Disease (DD). The method comprises the steps of identifying a subject suffering from DD, and administering to the subject an effective amount of rhamnolipid, optionally in combination with niclosamide or a salt thereof.

The present invention is also directed to a method for treating osteoarthritis. The method comprises the steps of identifying a subject suffering from osteoarthritis, and administering to the subject an effective amount of rhamnolipid, optionally in combination with niclosamide or a salt thereof.

The present invention is also directed to a method for adhesive capsulitis. The method comprises the steps of identifying a subject suffering from adhesive capsulitis, and administering to the subject an effective amount of rhamnolipid, optionally in combination with niclosamide or a salt thereof.

"Treating", as used herewith, means ameliorating the condition or reducing the symptoms of the disease, reducing the incidence and severity of the disease, inhibiting the progression of the disease, and/or inhibiting the development and progression in severity of contractions, nodes or cords associated with DD.

In the above treatment methods, rhamnolipids/niclosamide can be the only active ingredient(s), or rhamnolipids/niclosamide can be used together with another active ingredient that is useful for the treatment.

"An effective amount," as referred to in the above methods, is the amount effective to treat a disease by ameliorating the condition or reducing the symptoms of the disease.

Patients with Dupuytren's disease are affected by discomfort in the palmar area of the hand due to the development of firm nodules and cords in the palmar fascia. The disease causes the progressive loss of motion of the adjacent digits which results in significant limitations of daily living including feeding and self-care. The present method is effective in reducing expression of TGF-$\beta$ and pro-inflammatory cytokines and mediators such as IL-1$\alpha$, STAT3 and NF-kB, thus decreasing inflammation and progression of disease in DD. The present method is effective in improving one or more of the pathologic conditions associated with DD including nodule hardness, nodule size and vascularity and may result in the relaxation or rupture of the DD cord whereby the finger flexure caused by the cord is ameliorated.

Patients with osteoarthritis are affected by pain, swelling and loss of motion associated with the destruction of articular cartilage and the resulting release of pro-inflammatory cytokines such as IL-1$\alpha$. Along with the development of periarticular osteophytes causing loss of joint motion, these cytokines also cause loss of joint mobility as a consequence of joint inflammation. This inflammation results in pain and limitation of function such as walking in the case of osteoarthritis of the knee and hip, or pain and limitation of function such as lifting and self-care in the case of osteoarthritis of the shoulder. The present method is effective in reducing expression of TGF-$\beta$ and pro-inflammatory cytokines and mediators such as IL-1$\alpha$, STAT3 and NF-kB, thus decreasing inflammation and progression of disease in osteoarthritic joints. The present method is effective in improving one or more of the pathologic conditions associated with osteoarthritis including cartilage destruction, joint stiffness, effusion and capsular inflammation. Improvement will be evidenced by improvement in functional activities such as stair climbing and can be measured by functional measures such as decreased sit to stand time.

Patients with adhesive capsulitis of the shoulder are affected by progressive pain and limitation of motion of the affected joint. The onset may occur with or without antecedent trauma. There is a two four times increased prevalence of adhesive capsulitis in the diabetic population (Tighe C B et al, Southern Medical Journal, 2008, 101(6):591-595). This may be a consequence of underlying inflammation associated with diabetes mellitus. The inflammatory process associated with adhesive capsulitis is a result of many of the same proinflammatory cytokines seen in Dupuytren's disease and osteoarthritis. The present method is effective in reducing expression of TGF-$\beta$ and pro-inflammatory cytokines and mediators such as IL-1$\alpha$, STAT3 and NF-kB, thus decreasing inflammation and progression of disease in adhesive capsulitis. The present method is effective in improving one or more of the pathologic conditions associated with adhesive capsulitis including capsular inflammation and capsular contracture. Improvement will be evidenced by improved ability to reach overhead and away from the body as well as improved toileting functions, especially if the disease occurs in the dominant arm.

The pharmaceutical composition of the present invention can be applied by systemic administration. Systemic administration includes injection, topical, oral, intranasal, subcutaneous, percutaneous, intravenous administration, and other systemic routes of administration. Injection and topical administration are the preferred routes of administration. In a preferred embodiment, the pharmaceutical composition is injected into the affected area or into the surrounding tissue of a patient, or administered topically to affected areas of a patient.

In one embodiment, the pharmaceutical composition is administered by injection into affected areas of a patient.

In one embodiment, the method treats Dupuytren's disease and the pharmaceutical composition is administered by injection into affected areas of the hand of a patient.

In one embodiment, the method treats osteoarthritis or adhesive capsulitis, and the pharmaceutical composition is administered by periarticular injection or intraarticular injection.

In one embodiment, the pharmaceutical composition is administered topically to affected areas of the patient. For example, the pharmaceutical composition is administered topically to affected areas of the hand of a patient having a Dupuytren's disease. For example, the pharmaceutical composition is administered topically to the affected joint of a patient having osteoarthritis or adhesive capsulitis.

In one embodiment, the pharmaceutical composition is applied 1-3 times daily, 1-2 times daily, once daily, once every 2-3 days, once weekly, once every 2 weeks, once every 4 weeks, or once every 1-6 months by subcutaneous injection into the affected areas such as palpable cords of the hand. For an injection solution, the rhamnolipid concentration is in the range of 0.1%-30% w/v, preferably 0.5-10% w/v, 0.5-20% w/v, 1-10% w/v, 1-20% w/v, 2-10% w/v, or 2-20% w/v. The injection solution may further comprise niclosamide, which is both dissolved and evenly distributed within the rhamnolipid solution as a suspension of fine and barely visible particles at a concentration of 0.01-2 mg/mL. The total volume for injection is about 0.25-5 mL for the hand, about 0.5-10 mL for the knee, and about 0.5-20 mL for the shoulder, for one dosing, which can be injected several times to the target area.

In one embodiment, the pharmaceutical composition is topically applied 1-3 times daily.

In one embodiment, the pharmaceutical composition is administered topically using electroporation-enhanced drug absorption.

In one embodiment, the pharmaceutical composition is an oral formulation that is taken 1-4 times daily, once every 2-3 days, once weekly, once every 2 weeks, or once every 4 weeks.

In one embodiment, the pharmaceutical composition is an injectable formulation that is applied into affected areas of contracture (e.g., palpable cords) once and then repeated whenever contractions of the fingers or volume of the cords increases, or pain within the hand increases. Injections may be repeated once weekly, once every 2 weeks, or once every 4 weeks, 3, 6, 12, 24 or 36 months.

In another embodiment, a solid or semi-solid formulation in an extended release form is used. This application form is injected or otherwise inserted (e.g. during hand surgery) and slowly releases the active ingredients at a level that suppresses local collagen accumulation.

Those of skill in the art will recognize that a wide variety of delivery mechanisms are also suitable for the present invention.

The present invention is useful in treating a subject that is a mammal, such as humans, dogs and cats. The present invention is particularly useful in treating humans.

The following examples further illustrate the present invention. These examples are intended merely to be illustrative of the present invention and are not to be construed as being limiting.

EXAMPLES

Example 1. Oral Treatment of Rhamnolipids Reduced TGF-β and IL-1α Levels in Blood of Treated Mice This study evaluated TGF-β and IL-1a levels in a murine model. Diet-induced obese 14 weeks old, male C57BL/6 mice received daily oral administration of rhamnolipids. Body weight and overall health were monitored daily. Three groups of 8-9 mice received treatments for a total of 7 consecutive days.

Animal and Materials
Diet-Induced Obese (DIO) C57BL/6J male mice maintained with high fat diet. 12 weeks old at arrival.
  Diet: D12492 high fat diet
  Rhamnolipids: R95D90 (AGAE Technologies, Cornwallis OR). R95D90 is a solid-granular form of 95% pure rhamnolipids with 90% di-Rhamnolipid (primarily C10-C10)

Doses
Treatment Groups (8 mice per group)
  Di-rhamnolipid (DR) was added to water to produce a solution of 8 mg/ml and mixed in a 300 mL plastic bottle and stored in 4° C. refrigerator. The suspension is sonicated to prepare a homogenous suspension before each treatment.

DR High Dose (HD):
  Doses were escalated over the 7-day treatment phase. Sequential daily dose administrations were: 48 mg/kg, 96 mg/kg, 96 mg/kg, 96 mg/kg, 96 mg/kg, 144 mg/kg, 144 mg/kg. Mean dose was 103 mg/kg.

DR Low Dose (LD)
  Doses were escalated over the 7-day treatment phase. Sequential dose administrations were: 24 mg/kg, 48 mg/kg, 48 mg/kg, 48 mg/kg, 48 mg/kg, 72 mg/kg, 72 mg/kg. Mean dose was 51 mg/kg.

Matching Placebo
  Vehicle, no DR.

Blood samples were taken and TGF-β levels were measured by Eve Technologies Corporation, Calgary, AB. Canada) using TGF-β Multiplex Immunoassay. TGF-β1 is known to be elevated in both obesity and type 2 diabetes mellitus.

Statistical Analysis
  Analyses were performed via GraphPad T-tests. A p-value of <0.5 was viewed be viewed to be statistically significant.

Results
  FIG. 1 shows beneficial effects of di-rhamnolipids (DR) on TGF-β in blood of C57BL6 mice with diet-induced obesity after 7 days of oral dosing (mean daily dose for the LD group was 51 mg/kg and mean daily dose for the HD group was 103 mg/kg). The results show a dose dependent significant decrease in TGF-β blood level after 7 days of oral treatment with DR. placebo vs. high dose.

Figure 2:
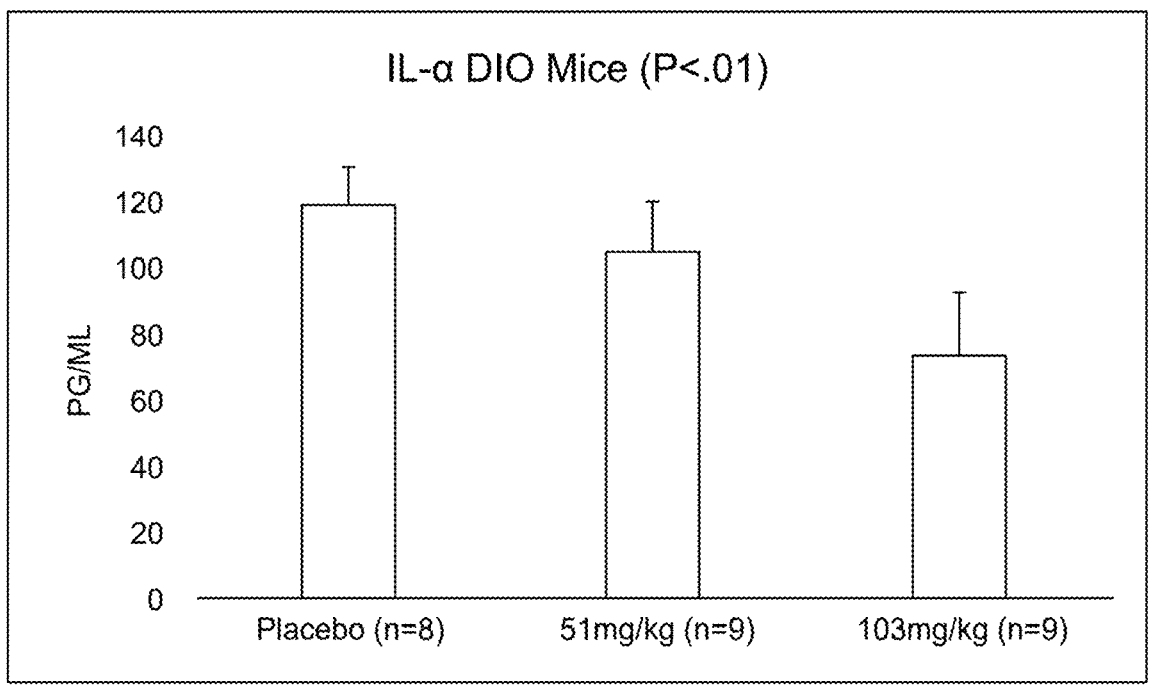
FIG. 2 shows a dose dependent significant decrease in IL-1a after 7 days of oral treatment with di-rhamnolipid). P<0.01 in placebo vs. high dose.

FIG. 2 shows a dose dependent significant decrease in IL-1a blood level after 7 days of oral treatment with DR. P<0.01 in placebo vs. high dose.

The results show that oral Treatment of rhamnolipids reduced TGF-β and IL-1α levels in blood of treated mice.

Example 2. Injected Rhamnolipid Solution Disputed Collagen in Minipig

Objective
  The objective of this study was to determine the effects of rhamnolipids when injected into dorsal subcutaneous fat pads in a minipig. The objectives were to test the tolerability of rhamnolipids by the minipig and the capability of rhamnolipids to lyse subcutaneous tissue (fatty tissue). The objectives further included determination of the degree of fibrous (collagen) bands within adipose tissue affected by the treatment and whether the treatment adversely affected surrounding tissues, especially muscle tissue and dermis.

Materials

Animal

One female minipig, 6 months old with a body weight of 23.5 kg.

Rhamnolipids

Di-rhamnolipid formulations at 0.25, 0.5, and 1.0 w/v in saline were prepared using R95D90 (AGAE Technologies, Cornwallis OR). R95D90 a solid-granular form of 95% pure rhamnolipids with 90% di-Rhamnolipid. NaCl (0.9%) was also used for the placebo injections.

Methods

Two 1 mL doses at 1 cm apart of the following concentrations were injected into dorsal subcutaneous tissue of a female minipig at a depth of 10 mm.

1) Placebo
2) 0.25% w/v
3) 0.5% w/v
4) 1.0% w/v

Statistical Analysis

Histology assessments were done by Histowiz (760 Parkside Avenue, Room 121 Advanced Biotechnology Park, Brooklyn, NY 11226). H&E stained histology slides were prepared and reviewed.

Results

Figure 3:
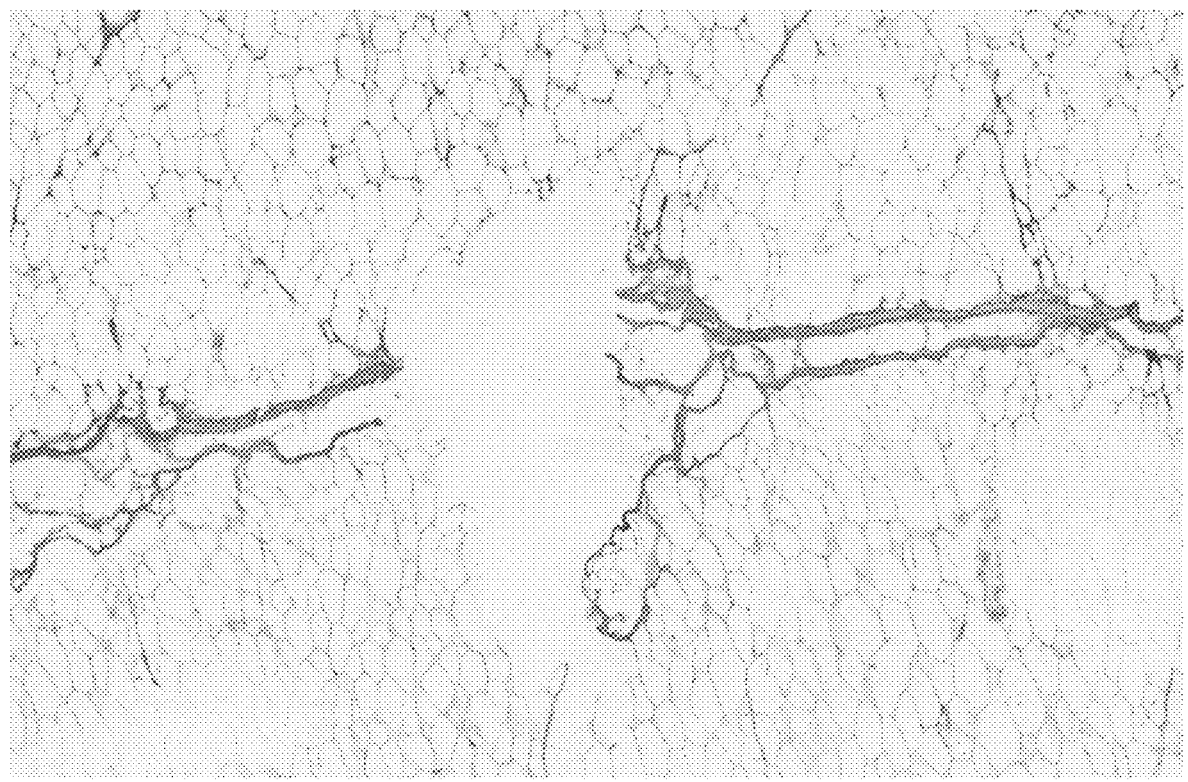
FIG. 3 shows the disruption of collagen bands within subcutaneous fatty tissues of a minipig injected with 0.5% (w/v) of a rhamnolipid formulation composed predominantly of di-rhamnolipid C10-C10.

FIG. 3 shows collagen disruption in subcutaneous adipose tissue after injection of 0.5% (w/v) rhamnolipids. This slide shows that adipocytes and fibrous bands that were disrupted by the injection of 0.5% w/v rhamnolipid solution as the injected rhamnolipid solution touched these fibrous bands predominantly consisting of collagen. Injection of 0.25% rhamnolipids showed a weaker results and injection of 1.0% showed a stronger reaction.

The overall conclusions are that rhamnolipid injections acutely lysed both adipocytes and adjacent fibrous tissues, but they did not affect underlying muscle tissues.

The results indicate that collagen structures can be disrupted by injecting rhamnolipids into the affected areas of the palmar regions of the hands of patients with Dupuytren's disease, or into selected areas of osteoarthritis and adhesive capsulitis.

Example 3. Improved Solubility of Niclosamide Ethanolamine in Aqueous Solutions of Rhamnolipids The solubility of niclosamide in aqueous solutions is poor without additional excipients. Rhamnolipids are bacterial glycolipids with surfactant properties that are highly soluble in aqueous solutions. This example shows that rhamnolipids improves the solubility of niclosamide in an aqueous solution.

Niclosamide Quantification

Niclosamide ethanolamine salt (niclosamide) was dissolved and titrated (2-fold) in methanol to generate standard curves. The linear range of niclosamide quantification using UV spectrometry (333 nm) was established to be 0.006-0.1 mM.

Niclosamide Solubility in the Presence of Rhamnolipid

A suspension of niclosamide was prepared in $H_2O$ at a concentration of 32.7 mg/ml (100 mM) by vigorous vortexing. A stock solution of rhamnolipids were prepared in $H_2O$ at a concentration of 400 mg/ml and diluted appropriately prior to the addition of niclosamide in the presence or absence of 20% glycerol. Niclosamide was added to a final concentration of 10 mM. The solutions were vortexed vigorously, warmed at 37° C. for 5 minutes, vortexed vigorously, and then centrifuged at 17,000 RCF for 5 minutes to remove any large particulates. The supernatant of each sample was assayed for soluble niclosamide by diluting 1:10 to 1:100 in methanol and comparing to a niclosamide standard curve.

Results

The results are summarized in Table 1.

TABLE 1

| Solubility of niclosamide in rhamnolipid solutions. | | | | | | |
|---|---|---|---|---|---|---|
| Rhamnolipid mg/mL (% w/v) | Glycerol % | Niclosamide ethanolamine mM | Particulates after centrifugation[A] | Soluble Niclosamide mM; ±SD[B] | Mg/mL | Increase solubility (%) |
| 0 | — | 10 | ***** | 1.06 ± 0.053 | 0.412 | N/A |
| 20 (2%) | — | 10 | **** | 2.26 ± 0.042 | 0.877 | 113 |
| 200 (20%) | — | 10 | *** | 3.74 ± 0.034 | 1.452 | 253 |
| 0 | 20 | 10 | ***** | 0.92 ± 0.023 | 0.357 | −13 |
| 20 (2%) | 20 | 10 | *** | 2.16 ± 0.032 | 0.838 | 104 |
| 200 (20%) | 20 | 10 | ** | 4.57 ± 0.034 | 1.774 | 331 |

[A]The quantity of precipitate after centrifugation was estimated by eye.
[B]Niclosamide concentration was determined from a standard curve The results show that Rhamnolipids can be used in an aqueous solution together with niclosamide to significantly improve the solubility of niclosamide. Rhamnolipid concentration (20% w/v) significantly increased solubility of niclosamide more than 3-fold. The achieved niclosamide concentrations exceed those that have been shown to significantly affect STAT3 and NF-kB, which are two factors associated with osteoarthritis.

Example 4. Treatment Protocol of Dupuytren's Contracture by Injections of Rhamnolipid into the Affected Palmar Region of the Hand Objectives To assess the clinical efficacy and tolerability of injections of rhamnolipids and rhamnolipids plus niclosamide, in patients with recurrence of contracture in hands.

Patient Population

Patients with recurrence of contracture after treatment with Xiaflex® or failure of needle aponeurectomy with affected digit(s) categorized as Tubiana class 2, 3 or 4 are eligible for the study.

Patients are screened and classified in accordance the Tubiana scale. If more than one joint of a finger is bent, the angles of contracture of each joint are added together. Patients are recruited if they are at least in stage 2 and present with documented progression of contractures by at least 10 degrees within the prior 6 months.

Figure 4:
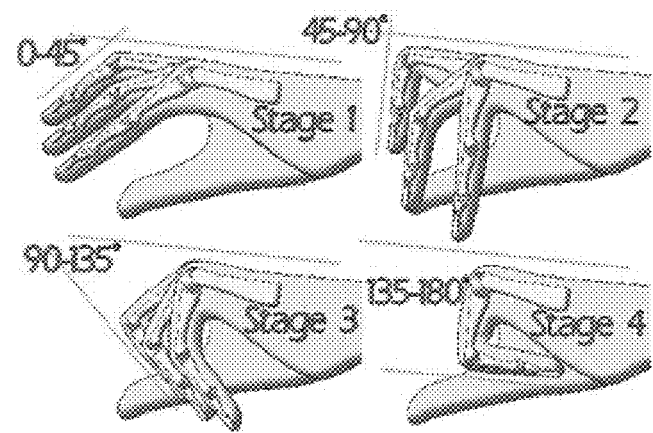
FIG. 4 shows various degrees of contracture of Dupuytren's Disease in a hand.

The index, middle, ring, and fifth digits have proximal, middle, and distal phalanges and three hinged joints: distal interphalangeal (DIP), proximal interphalangeal (PIP), and metacarpophalangeal (MCP). Total of the deficit of extension (MCP+PIP+DIP) is calculated in Table 2 and shown in FIG. 4.

TABLE 2

Stage Classification

| Stage | Contracture (Degrees) | Comment |
| --- | --- | --- |
| 0 | 0 | Healthy |
| N | 0 | Feel nodules/cords; nodule without deficit of extension |
| N/1 | 0-5 | Beginning contracture |
| 1 | 0-45 | Total of the deficit of extension (MCP + PIP + DIP) is between 0-45 degrees |
| 2 | 46-90 | Total of the deficit of extension (MCP + PIP + DIP) is between 45-90 |
| 3 | 91-135 | Total of the deficit of extension (MCP + PIP + DIP) is between 90-135 |
| 4 | >135 | Total of the deficit of extension (MCP + PIP + DIP) is >135 degrees |

Treatment
  Group 1: Patients receive Placebo (control)
  Group 2: Patients receive 2 mL 1% di-rhamnolipid solution.
  Group 3: Patients receive 2 mL 2% di-rhamnolipid solution.
  Group 4: Patients receive 2 mL of a solution containing 1% di-rhamnolipid and 1 mM niclosamide ethanolamine salt.
  Group 5: Patients receive 2 mL of a solution containing 2% di-rhamnolipid and 2 mM niclosamide ethanolamine salt.

Patients are treated once or twice/weekly injections in the first week and once weekly thereafter until 6 weeks are completed.

Reduction in progression and partial resolution of contracture are measured with a goniometer, which is a simple tool to measure the angle of bent fingers.

Range of motion of the metacarpophalangeal, proximal interphalangeal and distal phalangeal joints along with composite flexion of the affected digits are measured before treatment and weekly though week 6, and then at week 12.

Endpoint
  Significant differences in degrees of contracture in treated patients vs. control.

Example 5. Protocols for Treating Osteoarthritis

Objectives: To assess the clinical efficacy of intraarticular injections of rhamnolipids, rhamnolipids plus niclosamide, and hyaluronic acid (positive control) in patients with osteoarthritis (OA) of the knee.

Methods: This is a randomized, double-blind, 2-arm parallel design trial of a sufficient number of patients with radiologically confirmed knee OA. Two-milliliter intraarticular injections using 20 mg/mL hyaluronic acid sodium salt or rhamnolipid are administered weekly over 3 weeks.

Group 1: Patients receive 2 mL hyaluronic acid (positive control)
  Group 2: Patients receive 2 mL 1% di-rhamnolipid solution.
  Group 3: Patients receive 2 mL 2% di-rhamnolipid solution.
  Group 4: Patients receive 2 mL of a solution containing 1% di-rhamnolipid and 1 mM niclosamide ethanolamine salt.
  Group 5: Patients receive 2 mL of a solution containing 2% di-rhamnolipid and 2 mM niclosamide ethanolamine salt.

Patients are treated once or twice/weekly injections in the first week and once weekly thereafter until 6 weeks are completed.

Primary and Secondary Efficacy Assessment

The primary efficacy assessment including Western Ontario and McMaster Universities osteoarthritis index (WOMAC) score for knee pain is evaluated at the end of week 3.

Secondary efficacy assessments included WOMAC scores for knee pain at Weeks 6 and 12 (follow-up), as well as WOMAC stiffness, physical function and quality of life scores, visual analog scale (VAS) scores for pain at rest and following walking and stepping activity, range of knee joint motion, and global patient satisfaction with treatment and quality of life using the SF-36.

Results

After 3 weeks of study treatment, all five treatment groups are compared for improvements in knee function. Results from all other secondary efficacy assessments at Weeks 6 and 12 including patient satisfaction are performed.

Example 6. Protocols for Treating Adhesive Capsulitis

Objectives
  To assess the clinical efficacy of intraarticular injections of rhanmolipids, rhamnolipids plus niclosamide, and corticosteroid (positive control) in patients with adhesive capsulitis of the shoulder.

Method
  This is a randomized, double-blind, 2-arm parallel design trial of a sufficient number of patients with clinically confirmed adhesive capsulitis of the shoulder. Two-milliliter injections using 40 mg/ml triamcinolone acetate or rhamnolipid are administered in a single intra-articular injection,
  Group 1: Patients receive 2 mL of 40 mg/ml triamcinolone acetate (positive control)
  Group 2: Patients receive 2 mL 1% di-rhamnolipid solution.
  Group 3: Patients receive 2 mL 2% di-rhamnolipid solution.
  Group 4: Patients receive 2 mL of a solution containing 1% di-rhamnolipid and 1 mM niclosamide ethanolamine salt.
  Group 5: Patients receive 2 mL of a solution containing 2% di-rhamnolipid and 2 mM niclosamide ethanolamine salt.

Primary and Secondary Efficacy Assessments

The primary efficacy assessment is the Disabilities of the Shoulder, Arm and Hand (DASH) score. Range of motion is assessed pre-treatment and at 4 weeks post treatment. A standard physical therapy protocol is used post injection. Secondary efficacy assessments include comparison of percentage range of motion gained in the 6 primary planes of motion between the treatment groups Results After 4 weeks of study treatment, all three treatment groups are compared for improvements in DASH scores. Results from all other secondary efficacy assessments are compared among the three groups.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude the specification.

What is claimed is:

1. A method for treating Dupuytren's disease, osteoarthritis, or adhesive capsulitis, comprising administering to a patient in need thereof an effective amount of one or more rhamnolipids, wherein the rhamnolipids are selected from the group consisting of: α-L-rhamnosyl-β-hydroxydecanoyl-β-hydroxydecanoate, α-L-rhamnosyl-(1-2)-α-L-rhamnosyl-β-hydroxydecanoyl-β-hydroxydecanoate, α-L-rhamnopyranosyl-(1,2)-α-L-rhamnopyranosyl-β-hydroxydecanoyl-β-hydroxydodecanoate; α-L-rhamnopyranosyl-(1,2)-α-L-rhamnopyranosyl-β-hydroxytetradecanoyl-β-hydroxytetradecanoate, and a combination thereof.

2. The method according to claim 1, wherein the rhamnolipids are administered by injection into affected areas or surrounding tissues of the patient.

3. The method according to claim 2, wherein the method treats Dupuytren's disease, and the rhamnolipids are administered by injection into affected areas of the hand of the patient.

4. The method according claim 2, wherein the method treats osteoarthritis or adhesive capsulitis, and the rhamnolipids are administered by periarticular injection or intraarticular injection.

5. The method according to claim 1, wherein the rhamnolipids are administered topically to affected areas of the patient.

6. The method according to claim 5, wherein the method treats Dupuytren's disease, and the rhamnolipids are administered topically to affected areas of the hand of the patient.

7. The method according to claim 1, wherein the patient is further administered with niclosamide or a salt thereof.

8. The method according to claim 7, wherein the rhamnolipids and niclosamide are co-administered in one composition.

* * * * *